(12) United States Patent
Takasugi

(10) Patent No.: US 11,874,345 B2
(45) Date of Patent: Jan. 16, 2024

(54) MAGNETIC SENSOR AND METHOD OF MANUFACTURING SUCH, AND MAGNETIC DETECTION DEVICE AND MAGNETIC DETECTION SYSTEM

(71) Applicant: TDK Corporation, Tokyo (JP)

(72) Inventor: Keisuke Takasugi, Tokyo (JP)

(73) Assignee: TDK Corporation, Tokyo (JP)

( * ) Notice: Subject to any disclaimer, the term of this patent is extended or adjusted under 35 U.S.C. 154(b) by 0 days.

(21) Appl. No.: 17/078,315

(22) Filed: Oct. 23, 2020

(65) Prior Publication Data

US 2021/0123990 A1    Apr. 29, 2021

(30) Foreign Application Priority Data

Oct. 24, 2019   (JP) ................................. 2019-193629

(51) Int. Cl.
  *G01R 33/09* (2006.01)
  *G01N 33/543* (2006.01)
  *H10N 50/85* (2023.01)

(52) U.S. Cl.
  CPC ..... *G01R 33/093* (2013.01); *G01N 33/54326* (2013.01); *H10N 50/85* (2023.02)

(58) Field of Classification Search
  CPC .... G01R 33/093; G01R 33/025; G01R 33/93; G01N 33/54326; H01L 43/10
  See application file for complete search history.

(56) References Cited

U.S. PATENT DOCUMENTS

| | | | |
|---|---|---|---|
| 5,815,343 A * | 9/1998 | Ishikawa ............... | G11B 5/8404 |
| 7,564,659 B2 * | 7/2009 | Freitag ................ | G01R 33/093 |
| | | | 360/324.11 |
| 2007/0109692 A1 * | 5/2007 | Carey .................... | B82Y 10/00 |
| | | | 360/324.1 |
| 2008/0161200 A1 * | 7/2008 | Yu .......................... | C40B 40/08 |
| | | | 506/13 |

(Continued)

FOREIGN PATENT DOCUMENTS

| | | | | |
|---|---|---|---|---|
| JP | 2002107433 | * | 4/2002 | ............ G01R 33/06 |
| JP | 2002-237006 A | | 8/2002 | |
| JP | 5161459 B2 | | 6/2007 | |

(Continued)

OTHER PUBLICATIONS

An English machine translation of the Japanese Office Action dated Apr. 12, 2022 in corresponding JP patent application No. 2019-193629.

(Continued)

*Primary Examiner* — Alesa Allgood
(74) *Attorney, Agent, or Firm* — POSZ LAW GROUP, PLC

(57) ABSTRACT

A magnetic sensor used to detect a detection target substance in a sample includes a substrate having a first surface and a second surface, which is opposite the first surface and a magnetoresistive effect element provided on the first surface of the substrate. The resistance of the magnetoresistive effect element changes in accordance with an input magnetic field. A protective layer covers the top of the magnetoresistive effect element. The surface of the protective layer, which is positioned on top of the magnetoresistive effect element, has a prescribed surface roughness.

14 Claims, 7 Drawing Sheets

(56) References Cited

U.S. PATENT DOCUMENTS

2018/0299407 A1    10/2018   Haratani et al.
2019/0128882 A1     5/2019   Haratani et al.

FOREIGN PATENT DOCUMENTS

| JP | 6101215 B2 | 4/2014 |
|----|------------|--------|
| JP | 6043395 B2 | 9/2015 |
| WO | 2005/047864 A2 | 5/2005 |
| WO | 2009/086320 A1 | 7/2009 |
| WO | 2012/122536 A2 | 9/2012 |
| WO | 2017/082227 A1 | 5/2017 |
| WO | 2017/110534 A1 | 6/2017 |
| WO | 2017/170238 A1 | 10/2017 |

OTHER PUBLICATIONS

English machine translation of Chinese Office Action dated Sep. 23, 2023 in corresponding Chinese Patent Application No. 202011108663.7.

* cited by examiner

MAGNETIC SENSOR AND METHOD OF MANUFACTURING SUCH, AND MAGNETIC DETECTION DEVICE AND MAGNETIC DETECTION SYSTEM

The present application is based on and claims priority from Japanese Patent Application No. 2019-193629 filed on Oct. 24, 2019, the disclosure of which is incorporated herein by reference.

TECHNICAL FIELD

The present invention relates to a magnetic sensor and method of manufacturing such, and to a magnetic detection device and magnetic detection system.

BACKGROUND

As a quantitative immunoassay, radio immunoassay (RIA; immunoradiometric assay (IRMA)) is known. In this method, it is possible to label competitive antigens or antibodies and quantitatively measure antigens from measurement results of specific radioactivity, through radionuclides. Immunoassaying is a method of labeling target objects such as antigens or the like and accomplishing indirect measurement. This method is highly sensitive and thus makes significant contributions in clinical diagnoses but has the drawback that it is necessary to ensure radionuclide safety and thus designated facilities and devices are necessary. Hence, as a method that is easier to use, a method using a biosensor that uses magnetic beads or the like as indicators has been proposed (see Patent Literature 1~4).

A conventional biosensor is provided with a substrate, a magnetoresistance effect element such as a GMR element or the like provided on the substrate, and a protective film that covers the magnetoresistance effect element. When a magnetic field is applied after magnetic beads having an affinity for biomolecules in samples are captured in a protective layer via the biomolecules, a stray magnetic field is generated from the magnetic beads. The resistance value of the magnetoresistance effect element changes due to this stray magnetic field being input into the magnetoresistance effect element, and it is possible to indirectly detect the biomolecules based on this resistance value change.

PATENT LITERATURE

PATENT LITERATURE 1 Japanese patent 5161459
PATENT LITERATURE 2 Japanese patent 6043395
PATENT LITERATURE 3 Japanese patent 6101215
PATENT LITERATURE 4 International release 2017/82227 pamphlet

Problem to be Solved by the Invention

When the above-described biosensor is used in detecting biomolecules in a sample, the biomolecules are captured in the surface of the protective layer when a sample including the biomolecules that are the target of detection is caused to contact the biosensor. Furthermore, after magnetic beads and the biomolecules captured in the surface of the protective layer are caused to bond, excess biomolecules not captured in the protective layer and magnetic beads are selectively removed by a gradient magnetic field or washing or the like, and the resistance value change of the magnetoresistive effect element is measured.

However, in a conventional biosensor, a portion of the biomolecules captured in the protective layer and the magnetic beads are removed through application of a gradient magnetic field or washing or the like. Through this, there are cases in which the resistance value of the magnetoresistive effect element has difficulty making a sufficient change to detect the biomolecules, creating the problem that variance arises in detection results. In particular, in cases in which a sample having a low biomolecule concentration is used and this biomolecule is to be detected, the problem arises that variance in the detection results becomes large.

In consideration of the foregoing, it is an object of the present invention to provide a magnetic sensor having a magnetoresistive effect element capable of detecting with high accuracy substances that are the detection target using magnetic beads, and a method of manufacturing such, along with a magnetic detection device and a magnetic detection system.

Means for Solving the Problem

In order to resolve the above-described problems, the present invention provides a magnetic sensor used to detect a detection target substance in a sample, the magnetic sensor comprising a substrate having a first surface and a second surface, which is opposite the first surface; a magnetoresistive effect element provided on the first surface of the substrate. The resistance of the magnetoresistive effect element changes in accordance with an input magnetic field. A protective layer covers the top of the magnetoresistive effect element. The surface of the protective layer, which is positioned on top of the magnetoresistive effect element, has a prescribed surface roughness.

The lower limit of the mean roughness Ra of the surface of the protective layer can be 0.1 nm, and the upper limit of the mean roughness Ra is half the thickness of the protective layer on the magnetoresistive effect element. The thickness of the protective layer on the magnetoresistive effect element can be 3~200 nm. The mean roughness Ra can be 0.2~5.0 nm. A GMR element can be used as the magnetoresistive effect element. The detection target substance can be a biomolecule.

The present invention provides a magnetic detection device including the above-described magnetic sensor and a support unit that supports the magnetic sensor. A probe, which is capable of bonding specifically with the detection target substance, can be present on the surface of the protective layer.

The present invention provides a magnetic detection system including the above-described magnetic detection device, a magnetic field generation unit and a holding unit, which is capable of holding the sample. The magnetic detection device is provided such that the magnetic sensor can contact the sample held in the holding unit. The magnetic field generation unit is provided such that a magnetic field is applied on the magnetic sensor that contacts the sample held in the holding unit.

The present invention provides a method for producing a magnetic sensor used to detect a detection target substance in a sample. The magnetic sensor producing method includes: preparing a substrate having a first surface and a second surface, which is opposite the first surface; providing a magnetoresistive effect element on the first surface of the substrate, where the resistance of the magnetoresistive effect element changes in accordance with an input magnetic field; forming a protective layer that covers the top of the magnetoresistive effect element; and adjusting the surface of the protective layer, which is positioned on top of the magnetoresistive effect element, to a prescribed surface roughness.

The lower limit of the mean roughness Ra of the surface of the protective layer is 0.1 nm, and the upper limit of the mean roughness Ra is half the thickness of the protective layer on the magnetoresistive effect element. The mean roughness Ra of the surface of the protective layer can be adjusted to within a prescribed range by implementing a CVD process or polishing process on the surface of the protective layer, which is positioned on the magnetoresistive effect element. The thickness of the protective layer on the magnetoresistive effect element is 3~200 nm. The mean roughness Ra can be 0.2~5.0 nm. The magnetoresistive effect element can be a GMR element. The detection target substance can be a biomolecule.

EFFICACY OF THE INVENTION

With the present invention, it is possible to provide a magnetic sensor having a magnetoresistive effect element, which is capable of detecting with high accuracy substances that are the detection target using magnetic beads, and a method of manufacturing such, along with a magnetic detection device and a magnetic detection system.

BEST MODE FOR IMPLEMENTING THE INVENTION

Below, the best mode for implementing the magnetic sensor of the present invention is described with reference to the drawings. In this embodiment, the description takes as an example of a magnetic sensor a biosensor used in order to detect biomolecules as the substance that is target of detection, but this is intended to be illustrative and not limiting. The substance that is the target of detection that can be detected by the magnetic sensor may include, besides biomolecules, various organic compounds or the like such as volatile organic compounds (VOCs) or the like included in contaminated water or the like.

Figure 1:
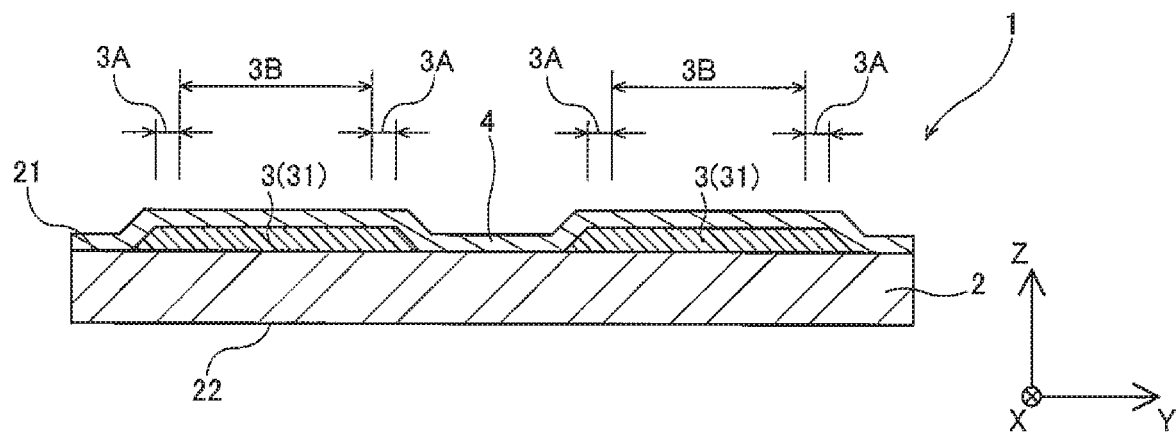
FIG. 1 is a cross sectional view showing the schematic configuration of a biosensor according to an embodiment of the present invention.
Figure 2A:
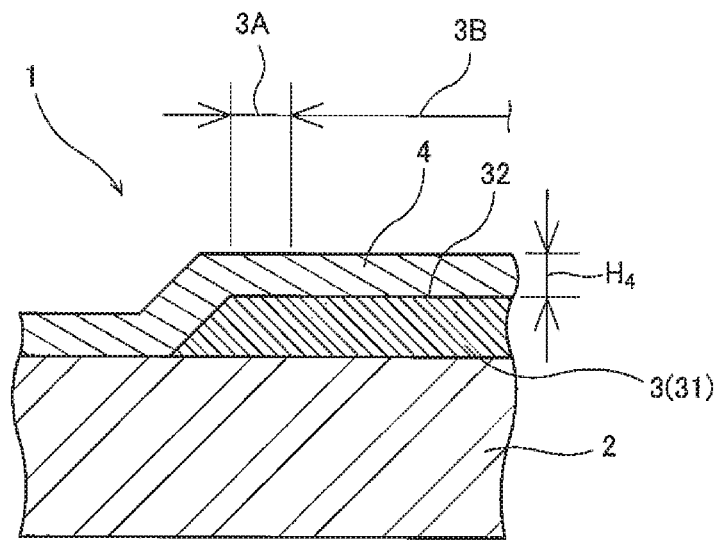
FIG. 2A is a partial enlarged cross sectional view showing the schematic configuration of a biosensor according to an embodiment of the present invention.
Figure 2B:
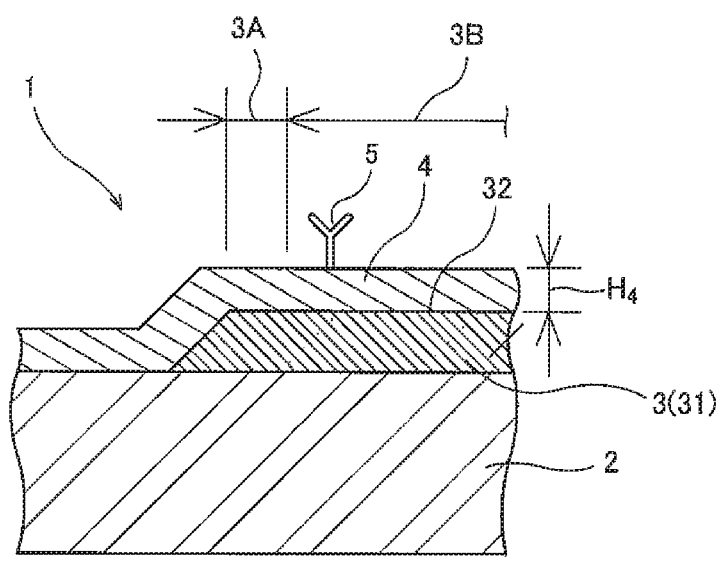
FIG. 2B is a partial enlarged cross sectional view showing the schematic configuration of a biosensor according to an embodiment of the present invention.
Figure 3:
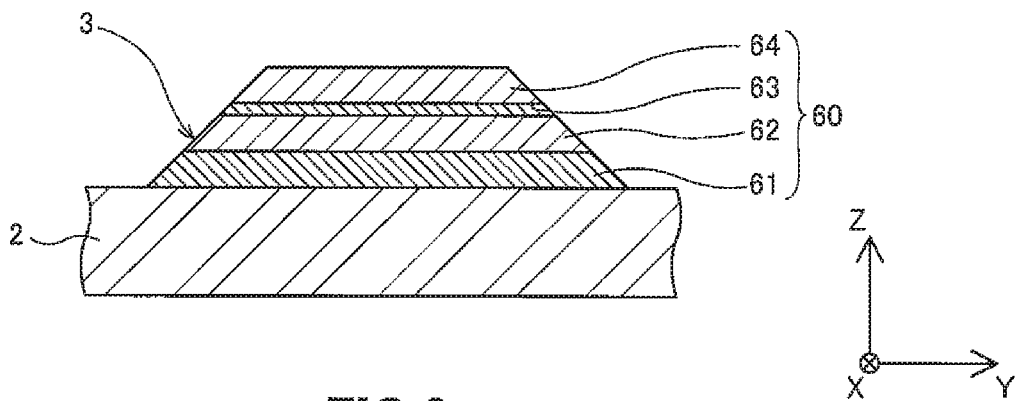
FIG. 3 is a cross sectional view showing the schematic configuration of a magnetoresistive effect element according to an embodiment of the present invention.
Figure 4:
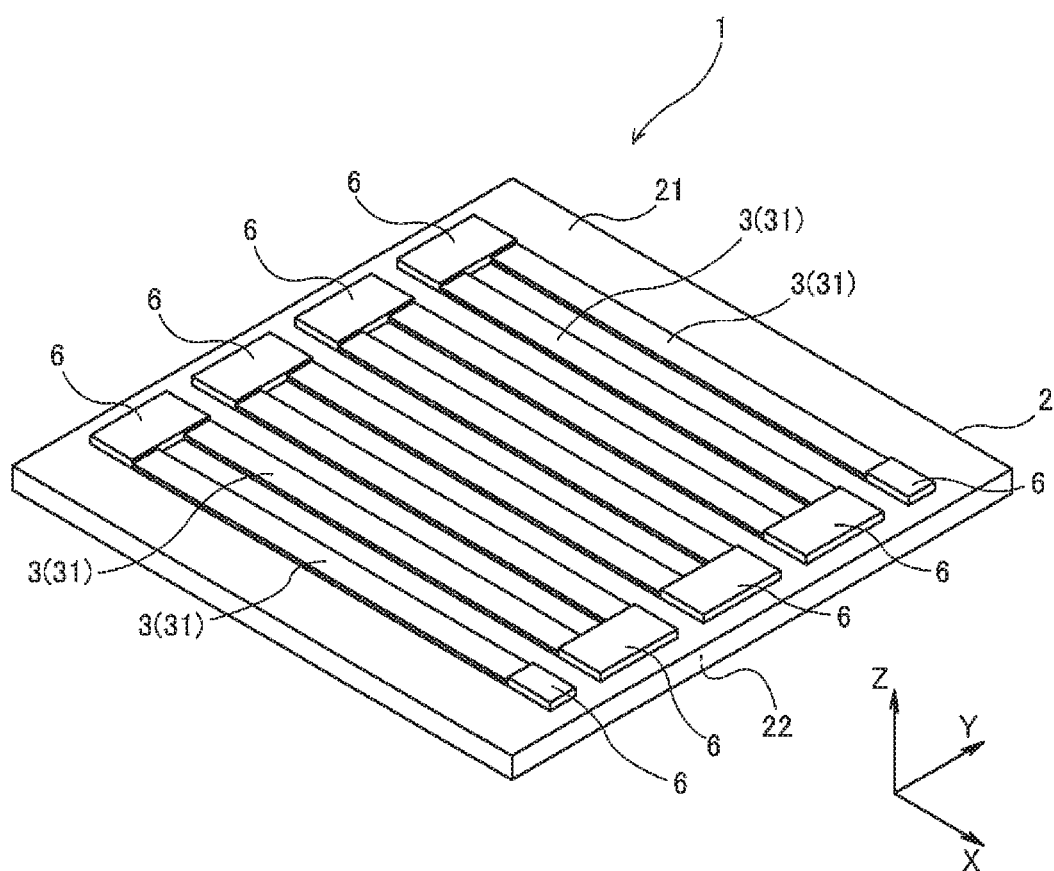
FIG. 4 is a perspective view showing the schematic configuration of the biosensor according to an embodiment of the present invention.

FIG. 1 is a cross sectional view showing the schematic configuration of a biosensor according to this embodiment, FIG. 2A and FIG. 2B are a partial enlargement cross sectional views showing the schematic configuration of the biosensor according to this embodiment, respectively, FIG. 3 is a cross sectional view showing the schematic configuration of a magnetoresistive effect element according to this embodiment, and FIG. 4 is a perspective view showing the schematic configuration of a biosensor according to this embodiment.

In the biosensor according to this embodiment, an "X-axis direction, Y-axis direction and Z-axis direction" are stipulated in a number of the drawings, as necessary. Here, the X-axis direction and the Y-axis direction are directions orthogonal to each other within the plane of a substrate in this embodiment (within a plane substantially parallel to a first surface and a second surface of the substrate), and the Z-axis direction is the direction of thickness of the substrate (the direction orthogonal to the first surface and the second surface of the substrate).

A biosensor 1 according to this embodiment includes a substrate 2 having a first surface 21 and a second surface 22, which is opposite to the first surface, a magnetoresistive effect element 3, which is provided on the first surface 21 of the substrate 2, and a protective layer 4, which covers the top of the magnetoresistive effect element 3. In the biosensor 1 according to this embodiment, by applying a magnetic field H on magnetic beads 10 that have accumulated biomolecules in a sample, captured in the protective layer 4 on the magnetoresistive effect element 3, it is possible to detect the biomolecules by detecting with the magnetoresistive effect element 3 a stray magnetic field Hs from the magnetic beads 10 (see FIG. 5).

The substrate 2 can be a rectangular one on which the magnetoresistive effect element 3 can be mounted, and among those that can be cited, for example, are a semiconductor substrate such as a silicon wafer or the like; a ceramic substrate such as AlTiC substrate, an alumina substrate or the like; a resin substrate; and a glass substrate or the like. An underlayer (omitted from the drawings) that includes $Al_2O_3$ or the like may be provided on the first surface 21 of the substrate 2 in accordance with the type of the substrate 2, and in particular, between the first surface 21 of the substrate 2 and the magnetoresistive effect element 3. The thickness of the substrate 2 can be appropriately set from the perspectives of the strength of the substrate 2 and making the biosensor 1 lightweight and thin but can be on the order of 5~100 nm, for example.

In this embodiment, a spin valve type of GMR element or the like can be used as the magnetoresistive effect element 3. The magnetoresistive effect element 3 has an MR layered body 60 that includes an antiferromagnetic layer 61, a magnetization fixed layer 62, a nonmagnetic layer 63 and a free layer 64, layered in that order from the substrate 2 side (see FIG. 3). The antiferromagnetic layer 61 is composed of an antiferromagnetic material and serves the role of fixing the direction of magnetization of the magnetization fixed layer 62 by causing exchange coupling with the magnetization fixed layer 62. The magnetoresistive effect element 3 can have a configuration in which the free layer 64, the nonmagnetic layer 63, the magnetization fixed layer 62 and the antiferromagnetic layer 61 are layered in that order from the substrate 2 side. In addition, the antiferromagnetic layer 61 may be omitted by the magnetization fixed layer 62 being a so-called self-pinned fixed layer (Synthetic Ferri Pinned layer, or SFP layer) having a layered ferri structure of a ferromagnetic layer/nonmagnetic intermediate layer/ferromagnetic layer and both ferromagnetic layers being antiferromagnetically coupled.

In the GMR element as the magnetoresistive effect element 3, the nonmagnetic layer 63 is a nonmagnetic conductive layer. In the GMR element, the resistance value changes in accordance with the angle formed by the direction of magnetization of the free layer 64 with respect to the direction of magnetization of the magnetization fixed layer 62, and the resistance value is a minimum when the angle is 0° (when the magnetization directions are parallel to each other) and the resistance value is a maximum when the angle is 180° (when the magnetization directions are antiparallel to each other).

The magnetoresistive effect element 3 is made in a meandering shape by a plurality of line-shaped sections 31 extending in the X-axis direction (first direction) being lined up in the Y-axis direction (second direction) and the ends of adjacent line-shaped sections being connected by lead electrodes 6 (see FIG. 4). In FIG. 4, depiction of the protective layer 4 has been omitted because such would make the drawing complicated.

A GMR element as the magnetoresistive effect element 3 in general has a relatively low element resistance value, so in order to cause a signal of prescribed strength to be output from the biosensor 1, it is necessary to make the linewidth of the GMR element narrow and the line length long. Furthermore, by comprising the GMR element in the above-described meandering shape, it is possible to make the linewidth of the GMR element narrow and the line length long within a limited region on the first surface 21 of the substrate 2. The lead electrodes can be made of one type of electroconductive material out of Cu, Al, Au, Ta, Ti or the like, for example, or a compound film of two or more electroconductive materials.

In the magnetoresistive effect element 3 composed of the above-described plurality of line-shaped sections 31, the magnetization direction of the magnetization fixed layer 62 is substantially parallel to the short direction of each line-shaped section 31. In the biosensor 1 according to this embodiment, by applying a magnetic field H in a direction orthogonal to the first surface 21 of the substrate 2 on the magnetic beads 10 captured in the protective layer 4 on the magnetoresistive effect element 3, a stray magnetic field Hs is generated from the magnetic beads 10 and applied on the magnetoresistive effect element 3 (see FIG. 5). By this stray magnetic field Hs being applied on the magnetoresistive effect element 3, the direction of magnetization of the free layer 64 changes, and through this, the resistance value of the magnetoresistive effect element 3 changes. By this change in resistance value being output as a signal, the existence and quantity of biomolecules in the sample can be detected in the biosensor 1.

The length of the line-shaped sections 31 in the longitudinal direction can be appropriately established in accordance with the size of the biosensor 1 as a whole and the sensitivity required of the biosensor 1, but for example can be on the order of 10~500 µm, and the length in the short direction can be on the order of 0.2~10 µm, for example.

In a planar view of the biosensor 1 according to this embodiment, each line-shaped section 31 of the magnetoresistive effect element 3 has a first region 3A positioned at the outer periphery of each of the line-shaped sections 31, and a second region 3B positioned inside the first region 3A to be encompassed by the first region 3A. The first region 3A is a region with a predetermined width (for example, on the order of 40 nm) facing toward the inside orthogonal to each of the edges, from each of the edges of the top surface 32 of each of the line-shaped sections 31. The upper limit of the width of the first region 3A in the short direction of the line-shaped sections 31 can be less than half of the width in the short direction of the top surface of each of the line-shaped sections 31 of the magnetoresistive effect element 3 and preferably on the order of 10% of the width in the short direction of the top surface of each of the line-shaped sections 31.

In this embodiment, the protective layer 4 that covers the entirety of the first surface 21 of the substrate 2 and the magnetoresistive effect element 3 is a layer in which biomolecules accumulated in the magnetic beads 10 can be captured. The biomolecules accumulated in the magnetic beads 10 may be captured in the protective layer 4 though an electrostatic interaction, a hydrogen bonding interaction or the like with the protective layer 4 or may be captured by a probe 5 (see FIG. 2B) provided on the surface of the protective layer 4 that is capable of bonding specifically with the biomolecules. The protective layer 4 may be made of a material that can exert an electrostatic interaction, a hydrogen bonding interaction or the like with a biomolecule, such as $SiO_2$, $Al_2O_3$, $Si_3N_4$, TiN, TaN, TaO, TiO, AlN or the like, for example. The surface of the protective layer 4, particularly the surface of the protective layer 4 located in the second region 3B of the magnetoresistive sensor 3, is specific to the biomolecule to be detected to easily capture the biomolecule. The surface of the protective layer may be provided with an affinity substance that can be bound to the target. The protective layer 4 may have a single-layer structure with one layer made of the above-described material or may have a multi-layer structure with two or more layers. When the protective layer 4 is a multi-layer structure, the material composing each of the layers of this multi-layer structure may be the same material or may be different materials.

The surface of the protective layer 4 has a prescribed surface roughness, and preferably, the mean surface roughness Ra of the surface of the protective layer 4 is at least 0.1 nm and not more than half of the thickness T4 of the protective layer 4, and more preferably, is 0.2~5.0 nm. Since the surface of the protective layer 4 is a surface having the prescribed surface roughness, it is difficult for the biomolecules and magnetic beads 10 captured in the protective layer 4 to be removed through the application of a gradient magnetic field or washing or the like. As a result, it is possible to detect with high accuracy the existence of and quantity of biomolecules. The mean surface roughness Ra of the surface of the protective layer 4 can be measured using an XE-3DM device (made by Park Systems Corp.), for example.

The surface of the protective layer 4 positioned at the second region 3B of the magnetoresistive effect element 3 has the above-described surface roughness, but the surface of the protective layer 4 positioned at the first region 3A may or may not have the above-described surface roughness. In the first region 3A of the magnetoresistive effect element 3 noise is readily superimposed through the stray magnetic field Hs from the captured magnetic beads 10. However, when the surface of the protective layer 4 positioned at the first region 3A of the magnetoresistive effect element 3 does not have the above-described surface roughness, it can be difficult to capture the biomolecules and magnetic beads 10 in the protective layer 4 positioned at the first region 3A of the magnetoresistive effect element 3, and it can be easy easy to remove the biomolecules and magnetic beads 10 captured in the protective layer 4 positioned at the first region 3A through the application of a gradient magnetic field or washing or the like.

The thickness T4 of the protective layer 4 can be appropriately set within a range such that the stray magnetic field Hs emitted from the magnetic beads 10 bonded to the biomolecules captured on the top surface of the protective layer 4 in the second region 3B can be applied on the magnetoresistive effect element 3. The thickness T4 of the protective layer 4 is set to around 3~200 nm, for example. When the protective layer 4 has a multi-layer structure (for example, a two-layer structure consisting of a first protective layer and a second protective layer), the thickness of the first protective layer positioned on the magnetoresistive effect element 3 is set to around 0.1~100 nm, for example, and the thickness of the second protective layer positioned on the first protective layer can be set to around 0.1~100 nm, for example.

By causing the biosensor 1 having the above-described configuration to come into contact with a sample that includes the biomolecules 11 that are the target of detection, it is possible to cause the biomolecules 11 to be captured in the surface of the protective layer 4. Furthermore, after the magnetic beads 10 and the biomolecules 11 captured in the surface of the protective layer 4 are caused to bond, the magnetic beads 10 and the biomolecules 11 that were not captured in the surface of the protective layer 4 on the magnetoresistive effect element 3 can be selectively removed through a gradient magnetic field or washing or the like. In this embodiment, by having the surface of the protective layer 4 on the magnetoresistive effect element 3 be a rough surface, it is possible to control removal of the magnetic beads 10 and the biomolecules 11 captured in the protective layer 4 by the application of a gradient magnetic field or washing or the like. That is to say, it is possible to easily and selectively remove, through a gradient magnetic field or washing or the like, the excess magnetic beads 10 and the biomolecules 11 not captured in the surface of the protective layer 4 on the magnetoresistive effect element 3.

Figure 5:
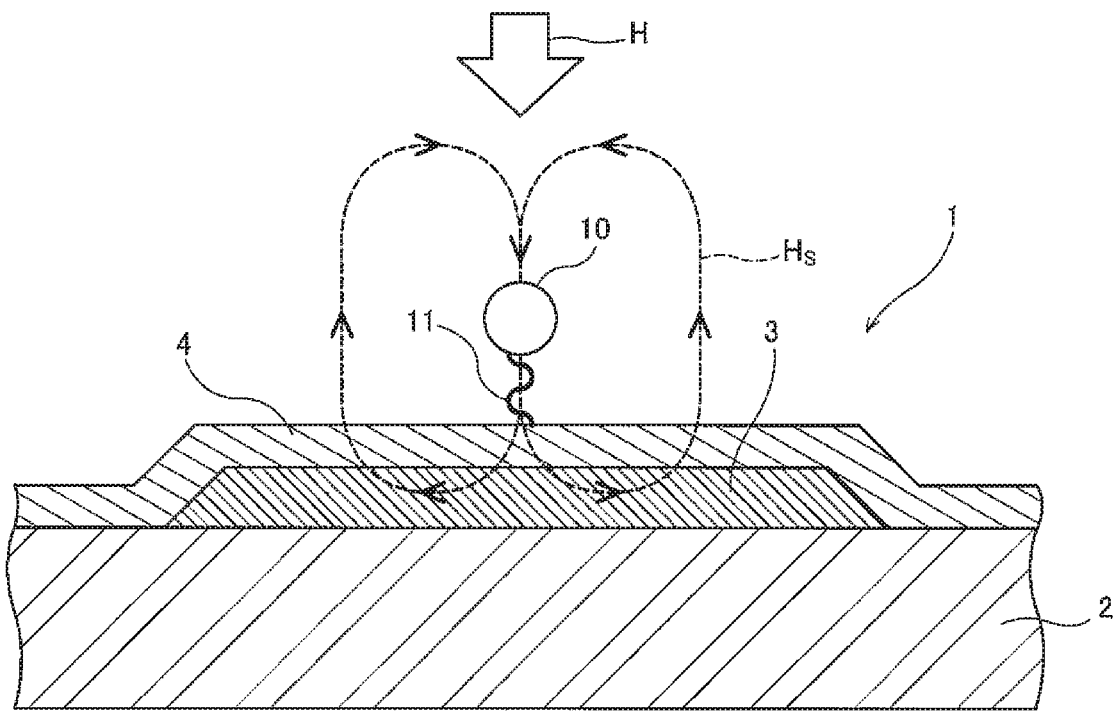
FIG. 5 is a cross sectional view for describing an overview of a biomolecule detection method using the biosensor according to an embodiment of the present invention.

As described above, after the biomolecules 11 and the magnetic beads 10 are left on the surface of the protective layer 4 on the magnetoresistive effect element 3, by applying a magnetic field H in a direction orthogonal to the first surface 21 of the substrate 2, the magnetic beads 10 take on magnetism and the stray magnetic field Hs is generated from the magnetic beads 10 (see FIG. 5). By this stray magnetic field Hs being applied on the magnetoresistive effect element 3, the magnetization direction of the free layer 64 changes and as a result the resistance value of the magnetoresistive effect element 3 changes. This resistance value change has a correlation (linear correlation) with the number of magnetic beads 10 bonded to the biomolecules 11 captured in the surface of the protective layer 5, so by this resistance value change being output from the biosensor 1 as a signal, it is possible to detect the presence of and the quantity of biomolecules that are the detection target in the sample.

As the biomolecules 11 that can be detected using the biosensor 1 according to this embodiment, the following can be listed, for example: nucleic acids such as DNA, mRNA, miRNA, siRNA, artificial nucleic acids (for example, Locked Nucleic Acid (LNA), Bridged Nucleic Acid (BNA) or the like) or the like (these may be naturally derived or chemically synthesized); peptides such as ligands, cytokines, hormones or the like; proteins such as receptors, enzymes, antigens, antibodies or the like; or cells, viruses, bacteria, fungi or the like.

In addition, as samples containing the biomolecules 11 that are the detection target, the following can be listed, for example: blood, blood serum, blood plasma, urine, buffy coat, saliva, semen, chest exudate, cerebrospinal fluid, tears, phlegm, mucus, lymph, abdominal fluid, pleural effusion, amniotic fluid, bladder lavage fluid, bronchoalveolar lavage fluid, cell extract fluid, cell culture supernatants and the like.

The magnetic beads can be particles capable of taking on magnetism, and for example, can be particles or the like made of gold, iron oxide or the like. The average particle diameter of the magnetic beads 10 can be on the order of 5~250 nm, for example, and preferably on the order of 20~150 nm. The average particle diameter of the magnetic beads 10 can, for example, be measured using a laser diffraction-type particle diameter distribution measurement device (product name: SALD-2300, made by Shimadzu Corp.).

The surface of the magnetic beads 10 may have fixed thereto a protein such as streptavidin or the like and may be further provided with an affinity substance capable of bonding specifically with the biomolecules. When used to capture ligands as the biomolecules 11, the magnetic beads 10 preferably have a hydrophilic surface, and when used to capture antibodies as the biomolecules 11, the magnetic beads 10 preferably have a hydrophobic surface.

With the biosensor 1 having the above-described configuration, by making the surface of the protective layer 4 on the magnetoresistive effect element 3 be a surface having the prescribed surface roughness (roughened surface), it becomes difficult for the magnetic beads 10 captured on the surface of the protective layer 4 to be removed by a gradient magnetic field or washing or the like. Consequently, with the biosensor 1 according to this embodiment, it is possible to detect the presence of and quantity of the biomolecules with high accuracy using the magnetic beads 10. Even if the biomolecules in the sample have a low concentration, it is possible to control variation in detection results and detect the presence of and quantity of the biomolecules with high accuracy.

The biosensor 1 having the above-described configuration can, for example, be produced as follows. FIGS. 6A~6F are process flow diagrams showing, in cross sectional view, the procedures of the method of manufacturing the biosensor 1 according to this embodiment.

An underlayer (omitted from drawings) that includes $Al_2O_3$ or the like is formed on a region that forms the magnetoresistive effect element 3 on the first surface 21 of the substrate 2, which is a semiconductor substrate such as a silicon wafer or the like, a ceramic substrate such as an AlTiC substrate, an alumina substrate or the like; a resin substrate; or a glass substrate or the like. The MR film 70 (a layered film with an antiferromagnetic film, a ferromagnetic film, a nonmagnetic film and a ferromagnetic film layered in that order) is formed through sputtering or the like on the first surface 21 of the substrate 2 (see FIG. 6A).

Figure 6A:
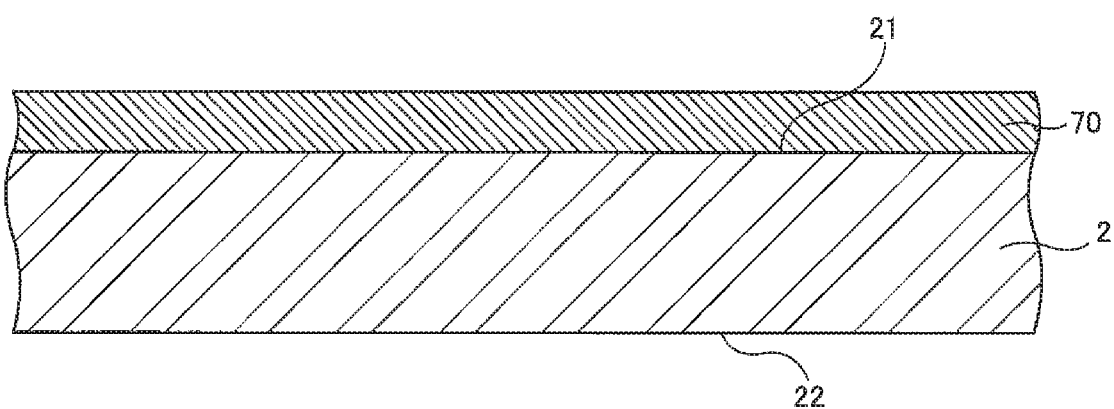
FIG. 6A is a cross sectional view showing one procedure out of the manufacturing procedures for the biosensor according to an embodiment of the present invention.
Figure 6B:
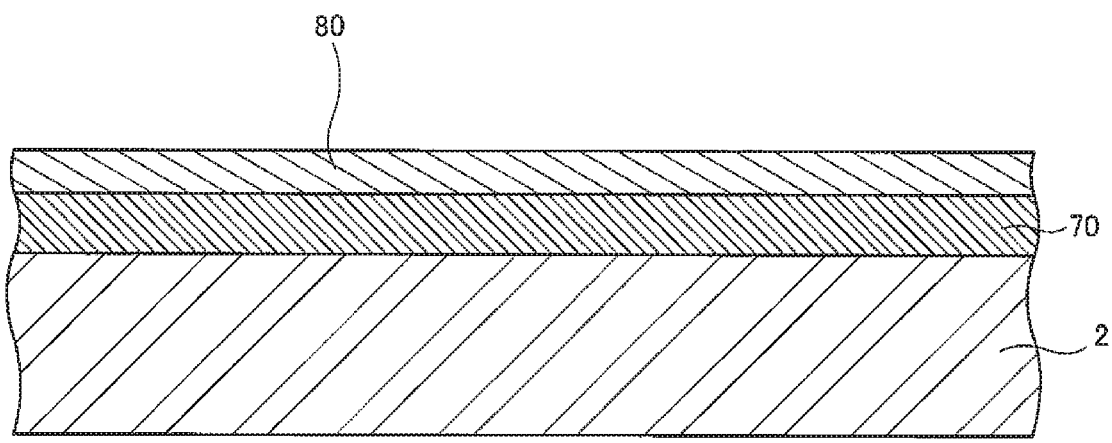
FIG. 6B is a cross sectional view showing the procedure that follows the procedure shown in FIG. 6A.
Figure 6C:
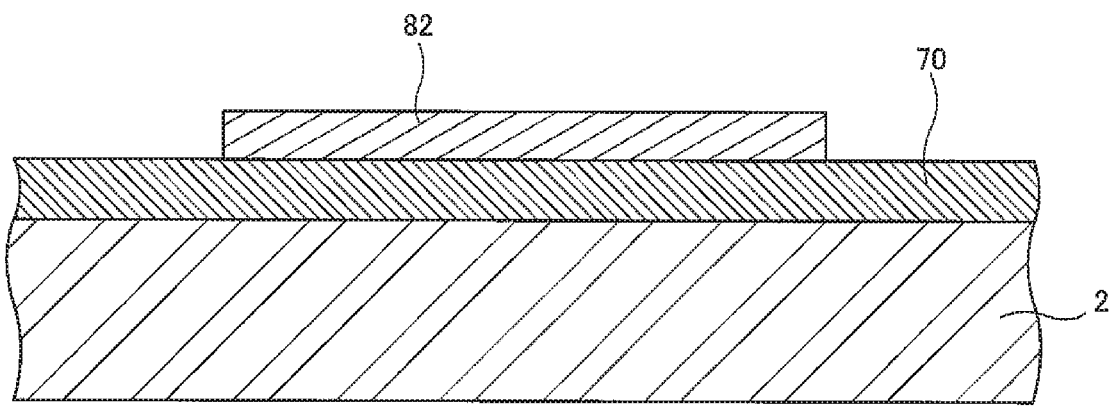
FIG. 6C is a cross sectional view showing the procedure that follows the procedure shown in FIG. 6B.

Next, a resist layer 80 covering the MR film 70 is formed (see FIG. 6B), and through an exposure/development process, a resist pattern 82 is formed, which corresponds to the magnetoresistive effect element 3 (see FIG. 6C). The resist material that makes up the resist layer 80 can be either a positive type or a negative type, and examples thereof include a cyclopentanone-class resist material and a novolac resin-class resist material or the like.

Figure 6D:
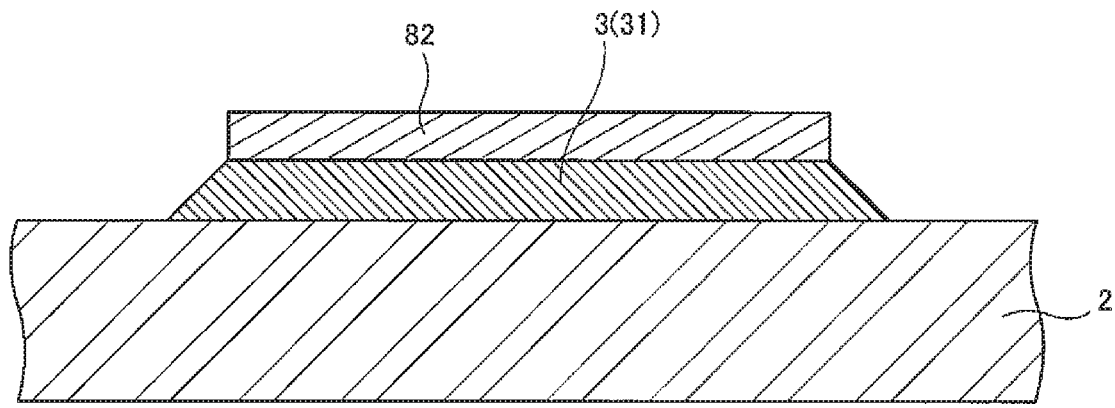
FIG. 6D is a cross sectional view showing the procedure that follows the procedure shown in FIG. 6C.
Figure 6E:
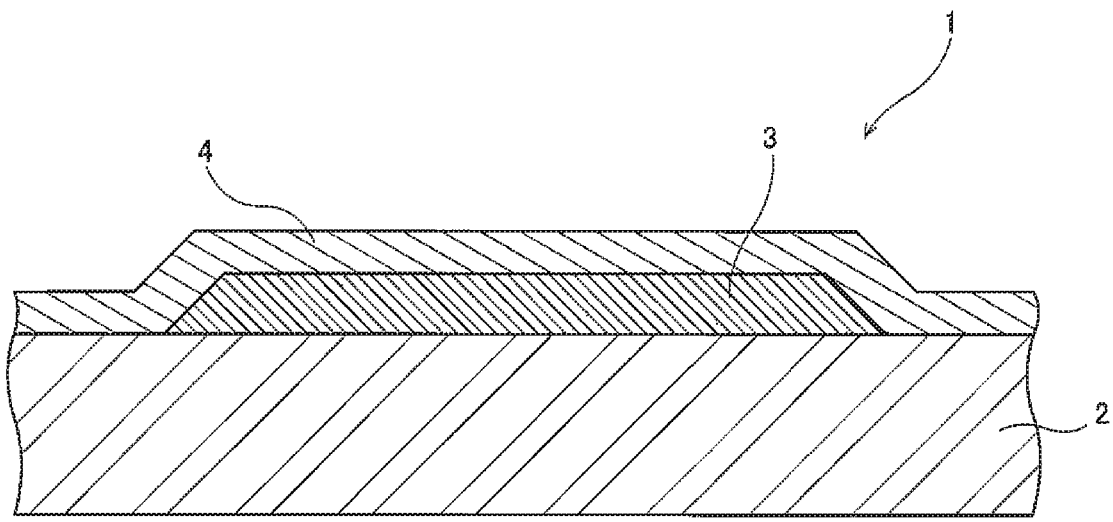
FIG. 6E is a cross sectional view showing the procedure that follows the procedure shown in FIG. 6D.

Next, after the MR film 70 has undergone a milling process with the resist pattern 82 as a mask, by applying a magnetic field while implementing a prescribed annealing process, the plurality of line-shaped sections 31 of the magnetoresistive effect element 3 is formed on the first surface of the substrate 2 (see FIG. 6D). The applied magnetic field can be appropriately set so that a prescribed exchange magnetic anisotropy is induced between the antiferromagnetic layer 61 and the magnetization fixed layer 62 in accordance with the effective vertical magnetic anisotropic energy Keff or the like given from the vertical magnetic anisotropic energy Ku and the shape anisotropic energy Kd of the magnetization fixed layer 62, the constituent materials of each layer and the film thickness, dimensions and shape of each layer of the magnetoresistive effect element 3.

Next, by forming the lead electrodes 6 that connect the ends of adjacent line-shaped sections 31 in the longitudinal direction through sputtering or the like of electroconductive materials, the magnetoresistive effect element 3 is formed. In addition, after the resist pattern 82 has been removed, the protective layer 4 that covers the first surface 21 of the substrate 2 and the magnetoresistive effect element 3 is formed by a CVD method, a PVD method such as reactive sputtering or the like, or a film formation method such as a vacuum deposition method or the like (see FIG. 6E).

A surface roughness adjustment process is accomplished on the surface of the protective layer 4 positioned on the magnetoresistive effect element 3 formed as described above in order to make the surface have the desired surface roughness. As a result, the biosensor 1 according to this embodiment can be manufactured.

Examples of the surface roughness adjustment process include a CVD process, a polishing process or the like on the surface of the protective layer 4. The mean roughness Ra of the surface of the protective layer 4 formed through the above-described film formation method (CVD method, PVD method, vacuum deposition process or the like) at times deviates from the prescribed range (not less than 0.1 nm and not more than half of the thickness T4 of the protective layer 4). The primary causes of this are thought to be that in the course of forming the magnetoresistive effect element 3 (MR film 70), the oxide film on the metal film exposed to the outermost surface of the magnetoresistive effect element 3 (MR film 70) grows, or the particles of the metal film grow, or unevenness is formed in the outermost surface of the magnetoresistive effect element 3 (MR film 70) by the washing process or peeling process. When the mean roughness Ra of the surface of the protective layer 4 deviates from the prescribed range, at least a portion of the biomolecules and magnetic beads 10 captured on the protective layer 4 are removed by the application of the gradient magnetic field or washing or the like, variation could arise in the detection results from the biosensor 1. However, in this embodiment, because the above-described surface roughness adjustment process is accomplished on the surface of the protective layer 4, it is possible make the mean roughness Ra of the surface of the protective layer 4 be within the prescribed range, and it is possible to control removal of the biomolecules and magnetic beads 10 captured on the protective layer 4 by the application of the gradient magnetic field or washing or the like, so highly accurate detection is possible. As the above-described surface roughness adjustment process, it is possible to adjust the mean roughness Ra of the surface of the protective layer 4 by adjusting the process conditions in the CVD process (for example, the film formation temperature, electrical discharge power and film formation pressure or the like) when accomplishing the CVD process on the surface of the protective layer 4.

Figure 7:
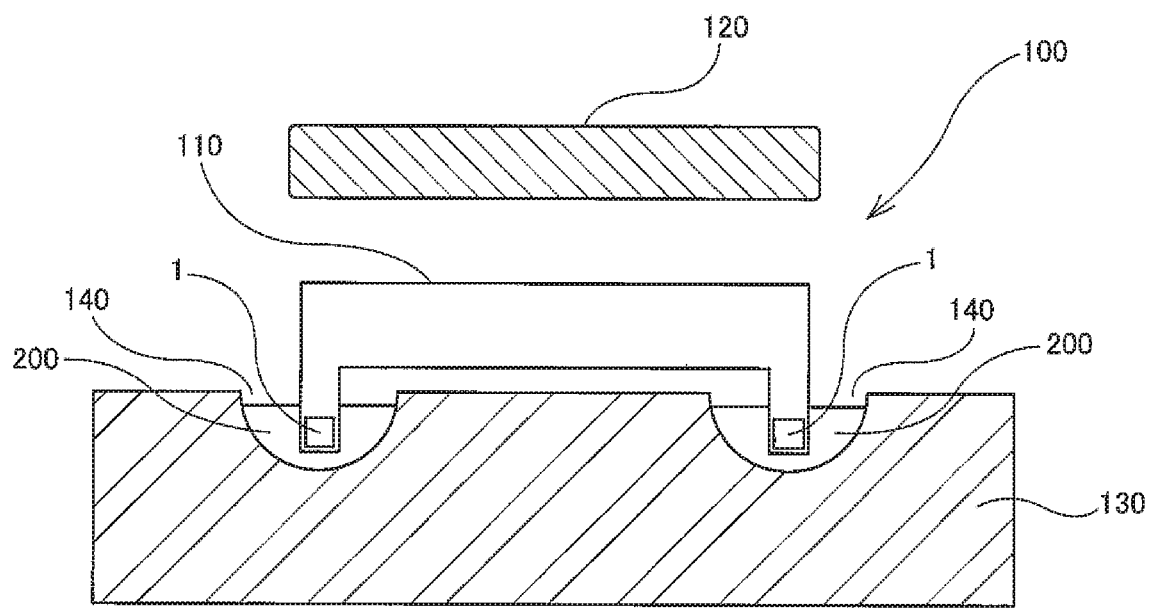
FIG. 7 is a cross sectional view showing the schematic configuration of a magnetic detection system according to the embodiment of the present invention.

A magnetic detection device using the biosensor 1 having the above-described configuration and a magnetic detection system provided with this magnetic detection device will be described. FIG. 7 is a cross sectional view showing the schematic configuration of a magnetic detection system according to this embodiment.

A magnetic detection system 100 in this embodiment is provided with a magnetic detection device having the biosensor 1 and a support unit 110 that supports this biosensor 1, a magnetic field generation unit 120 and a plate 130 having a plurality of reservoirs 140 that hold a sample 200 containing biomolecules.

A probe 5 (for example, a ligand or the like) that can bond specifically with the biomolecules in the sample 200 may be provided on the surface of the protective layer 4 of the biosensor 1 (see FIG. 2B). Naturally, the surface of the protective layer 4 of the biosensor 1 may also be configured so that the biomolecules are captured in the protective layer 4 by electrostatic interaction, hydrogen bonding interaction or the like, without the probe being provided on the surface of the protective layer 4 of the biosensor 1 (see FIG. 2A). The biomolecules in the sample 200 can be accumulated in the magnetic beads 10 (see FIG. 5). The support unit 110 that supports the biosensor 1 has a plurality of strip-shaped sections of a size capable of being inserted into each reservoir 140. When the tips of the strip-shaped sections are inserted into the reservoirs 140 the biosensor 1 is attached to the tip of each strip-shaped section so that the biosensor 1 is caused to contact the sample 200 housed in each reservoir 140. The support unit 110 is capable of raising and lowering. Thus, it is possible to insert each of the strip-shaped sections into each of the reservoirs 140 and to remove such from each of the reservoirs 140.

The magnetic field generation unit 120 is composed coils or the like that can generate a magnetic field in a direction orthogonal to the first surface 21 of the substrate 2 of the biosensor 1, for example, and are provided so that a magnetic field can be applied on the biosensor 1 when the biosensor 1 is caused to contact the sample 200 housed in each reservoir 140.

In the magnetic detection system 100 having this kind of configuration, when the biosensor 1 is caused to contact the sample 200 housed in each of the reservoirs 140, the biomolecules accumulated in the magnetic beads 10 (see FIG. 5) are captured in the protective layer 4 of the biosensor 1. In this state, when a magnetic field is generated in a direction orthogonal to the first surface 21 of the substrate 2 from the magnetic field generation unit 120, the magnetic beads 10 take on magnetism and the stray magnetic field Hs (see FIG. 5) is generated from the magnetic beads 10. By this stray magnetic field Hs being applied on the magnetoresistive effect element 3, the magnetization direction of the free layer 64 changes, and as a result, the resistance value of the magnetoresistive effect element 3 changes and a signal is output from the biosensor 1. The change in resistance value of the magnetoresistive effect element 3 has a correlation (linear correlation) with the number of magnetic beads 10 bonded to the biomolecules 11 captured in the surface of the protective layer 4, so in the magnetic detection system 100, the presence of and quantity of the biomolecules in the sample can be detected on the basis of the signal output from the biosensor 1.

In the above-described magnetic detection system 100, the magnetic field generation unit 120 causes a magnetic field to be generated in order to cause magnetization of the magnetic beads 10. In a state in which the biomolecules accumulated in the magnetic beads 10 are captured on the protective layer 4 of the biosensor 1, an alternating current magnetic field may be caused to be generated in the in-plane direction (the in-plane direction of the XY plane) of the magnetoresistive effect element 3. In the magnetic detection system 100 of this aspect, first the biosensor 1 is caused to make contact with the sample 200 housed in each of the reservoirs 140 and the magnetic beads 10 are magnetized by the magnetic field generated from the magnetic field generation unit 120. In addition, the biomolecules accumulated in the magnetized magnetic beads 10 are captured in the protective layer 4 of the biosensor 1. In this state, when the aforementioned alternating current magnetic field is caused to be generated from the magnetic field generation unit 120, the stray magnetic field is generated from the magnetic beads 10. By this stray magnetic field being applied on the magnetoresistive effect element 3, the magnetization direction of the free layer 64 changes and as a result the resistance value of the magnetoresistive effect element 3 changes and a signal is output from the biosensor 1.

The embodiment described above was discussed in order to facilitate understanding of the present invention and is intended to be illustrative and not limiting. Accordingly, each component disclosed in the above-described embodiment shall be construed to include all design modifications and equivalents that fall within the technical scope of the present invention.

In the above-described embodiment, only the mean roughness Ra of the surface of the protective layer 4 positioned on the magnetoresistive effect element 3 (line-shaped section 31) may be adjusted to within the prescribed range, or only the mean roughness Ra of the surface of the protective layer 4 positioned on the second region 3B of the magnetoresistive effect element 3 (line-shaped section 31) may be adjusted to within the prescribed range. For example, it is possible to form a resist pattern having an aperture that causes exposure of only the protective layer 4 positioned on the second region 3B of the magnetoresistive effect element 3 and to reduce the mean roughness Ra of the surface of the protective layer 4 by implementing an ion mining process at a low angle with respect to the protective layer 4 exposed from the aperture of this resist pattern and to thereby adjust the mean roughness Ra to within the above-described prescribed range. In addition, it is possible to reduce the mean roughness Ra of the surface of the protective layer 4 and to thereby adjust the mean roughness Ra to within the above-described prescribed range by forming an insulating film through a CVD method or the like on the protective layer 4 exposed from the aperture of the above-described resist pattern. Furthermore, it is possible to increase the mean roughness Ra of the surface of the protective layer 4 and to thereby adjust the mean roughness Ra to within the above-described prescribed range by causing a prescribed chemical solution (for example, buffered hydrofluoric acid or the like) to make contact with the surface of the protective layer 4 exposed from the aperture of the above-described resist pattern and to cause the grain boundary of the material comprising the protective layer 4 to appear. Further, it is possible to form a thin film by accomplishing sputtering or the like, in which the particle diameter of the target particles of $Al_2O_3$, $SiO_2$, SiN or the like has been adjusted, on the surface of the protective layer 4 exposed from the aperture of the above-described resist pattern and, through this, to adjust the particle diameter of the particles comprising the thin film and to adjust the mean roughness Ra of the surface of the thin film to within the above-described prescribed range. It is possible to adjust only the mean roughness Ra of a specific region (the region on the line-shaped section 31 or the region on the second region 3B of the line-shaped section 31) on the surface of the protective layer 4.

EMBODIMENTS

Below, the present invention will be described in greater detail through embodiments or the like, but the present invention is in no way limited by the below-described embodiments or the like.

Test Example 1

Various samples of the biosensor 1 having the configuration shown in FIG. 1 and having 90 of the magnetoresistive effect elements 3 were prepared, with the thickness T4 of the protective layer 4 in the second region 3B of the magnetoresistive effect elements 3 set at 30 nm and each of the samples having a different mean roughness Ra of the surface of the protective layer 4 (Samples 1~9; the mean roughness Ra (nm) of each sample is shown in Table 1). Specifically, the mean roughness Ra of the surface of the protective layer 4 in each of the samples was adjusted by accomplishing a CVD process on the protective layer (using tetraethoxysilane (TEOS) as the raw material gas) and adjusting the film formation temperature, electrical discharge power and film formation pressure in this CVD process. For each sample, the resistance change ratio R (the change ratio with reference to the resistance value of the magnetoresistive effect element 3 prior to capture of the magnetic beads 10 (zero magnetic field)) of the magnetoresistive effect element 3 in a state in which magnetic beads 10 were captured in the protective layer 4 was found, and the value ($R/C_{MIN}$) found by dividing the resistance change ratio R by the minimum value $C_{MIN}$ of the sample concentration detectable by the magnetoresistive effect element 3 was calculated. Results are shown in Table 1. The minimum value $C_{MIN}$ of the detectable sample concentration was found as the minimum sample concentration at which the correlation between the sample concentration and the resistance change value was lost. In addition, the results ($R/C_{MIN}$) shown in Table 1 are relative values when the values ($R/C_{MIN}$) of Sample 3 and Sample 4 are 1. If the value $R/C_{MIN}$ is 0.3 or greater, it is possible to say that this is acceptable as inspection sensitivity.

In addition, in each of the above-described samples (Samples 1~9), the variation (detection variation, %) of the resistance change ratio R of each of the 90 magnetoresistive effect elements 3 was found and each sample was evaluated on the basis of this detection variation. Results are shown in Table 1. In Table 1, "⊚" indicates that the detection variance was less than 5%, "○" indicates that the detection variation was 5%, and "X" indicates that the detection variation was in excess of 5%.

TABLE 1

|  | Ra (nm) | $R/C_{MIN}$ | Detection variation | Protective layer film formation |
|---|---|---|---|---|
| Sample 1 | 0.01 | 0.25 | ⊚ | X |
| Sample 2 | 0.1 | 0.75 | ⊚ | X |
| Sample 3 | 0.2 | 1 | ⊚ | ○ |
| Sample 4 | 0.5 | 1 | ⊚ | ⊚ |
| Sample 5 | 1.0 | 0.67 | ⊚ | ⊚ |

TABLE 1-continued

|  | Ra (nm) | R/C$_{MIN}$ | Detection variation | Protective layer film formation |
|---|---|---|---|---|
| Sample 6 | 3.0 | 0.45 | ◎ | ◎ |
| Sample 7 | 5.0 | 0.41 | ◎ | ◎ |
| Sample 8 | 15.0 | 0.37 | ○ | ◎ |
| Sample 9 | 30.0 | 0.36 | X | ◎ |

As is clear from the results shown in Table 1, by having the mean roughness Ra of the surface of the protective film 4 be within the prescribed range (not less than 0.1 nm and not greater than 15 nm), it was confirmed that it is possible to detect with high accuracy the biomolecules 11 in the sample using the magnetic beads 10. Even using samples with extremely low concentrations, it was confirmed that detection of the biomolecules 11 was possible with high accuracy. In addition, it was confirmed that by having the mean roughness Ra of the surface of the protective layer 4 be not more than 5.0 nm, it was possible to further reduce the detection variation of the biomolecules 11 in each of the plurality of magnetoresistive effect elements 3 with which the biosensor 1 is provided.

DESCRIPTION OF SYMBOLS

1 Biosensor
2 Substrate
21 First surface
22 Second surface
3 Magnetoresistive effect element
31 Line-shaped section
3A First region
3B Second region
4 Protective layer

The invention claimed is:

1. A magnetic sensor used to detect a detection target substance in a sample, the magnetic sensor comprising:
   a substrate having a first surface and a second surface, which is opposite the first surface;
   a magnetoresistive effect element provided on the first surface of the substrate, wherein the resistance of the magnetoresistive effect element changes in accordance with an input magnetic field; and
   a protective layer that covers the magnetoresistive effect element;
   wherein a surface of the protective layer, which is positioned on top of the magnetoresistive effect element, has a prescribed surface roughness, and
   a lower limit of a mean roughness Ra of the surface of the protective layer is 0.1 nm, and an upper limit of the mean roughness Ra is half a thickness of the protective layer on the magnetoresistive effect element.

2. The magnetic sensor according to claim 1, wherein a thickness of the protective layer on the magnetoresistive effect element is 3~200 nm.

3. The magnetic sensor according to claim 1, wherein a mean roughness Ra of the protective layer is 0.2~5.0 nm.

4. The magnetic sensor according to claim 1, wherein the magnetoresistive effect element is a GMR element.

5. The magnetic sensor according to claim 1, wherein the detection target substance is a biomolecule.

6. A magnetic detection device comprising:
   the magnetic sensor according to claim 1; and
   a support unit that supports the magnetic sensor.

7. The magnetic detection device according to claim 6, wherein a probe, which is capable of bonding specifically with the detection target substance, is present on the surface of the protective layer.

8. A magnetic detection system comprising:
   the magnetic detection device according to claim 6;
   a magnetic field generation unit; and
   a holding unit capable of holding the sample;
   wherein the magnetic detection device is provided such that the magnetic sensor can contact the sample held in the holding unit; and
   the magnetic field generation unit is provided such that a magnetic field is applied on the magnetic sensor, which contacts the sample held in the holding unit.

9. A method for producing a magnetic sensor used to detect a detection target substance in a sample, the magnetic sensor manufacturing method including:
   preparing a substrate having a first surface and a second surface, which is opposite the first surface;
   providing a magnetoresistive effect element on the first surface of the substrate, wherein the resistance of the magnetoresistive effect element changes in accordance with an input magnetic field;
   forming a protective layer that covers the magnetoresistive effect element; and
   adjusting a surface of the protective layer, which is positioned on top of the magnetoresistive effect element, to a prescribed surface roughness;
   wherein a lower limit of a mean roughness Ra of the surface of the protective layer is 0.1 nm, and an upper limit of the mean roughness Ra is half a thickness of the protective layer on the magnetoresistive effect element.

10. The magnetic sensor producing method according to claim 9, wherein a mean roughness Ra of the surface of the protective layer is adjusted to within a prescribed range by implementing a CVD process or polishing process on the surface of the protective layer, which is positioned on the magnetoresistive effect element.

11. The magnetic sensor producing method according to claim 9, wherein the protective layer is formed such that a thickness of the protective layer on the magnetoresistive effect element is 3~200 nm.

12. The magnetic sensor producing method according to claim 9, wherein a mean roughness Ra of the protective layer is 0.2~5.0 nm.

13. The magnetic sensor producing method according to claim 9, wherein the magnetoresistive effect element is a GMR element.

14. The magnetic sensor producing method according to claim 9, wherein the detection target substance is a biomolecule.

* * * * *